United States Patent
Hill et al.

[11] Patent Number: 6,117,115
[45] Date of Patent: Sep. 12, 2000

[54] MEDICAL TUBING SLIDE CLAMP DEVICE FOR DETERMINING PROPER TUBING SIZE AND FUNCTIONAL CHARACTERISTICS

[75] Inventors: Roger J. Hill, Richardson; James H. Monti, Jr., Plano; David J. Harrison, Irving, all of Tex.

[73] Assignee: B. Braun Medical, Inc., Bethlehem, Pa.

[21] Appl. No.: 09/169,901

[22] Filed: Oct. 12, 1998

[51] Int. Cl.[7] ............................................. A61M 5/00
[52] U.S. Cl. .............................. 604/250; 604/65; 604/67
[58] Field of Search ............................... 604/33, 34, 246, 604/249, 250, 256, 65, 67; 81/9.3; 29/243.56; 251/4, 7, 10

[56] References Cited

U.S. PATENT DOCUMENTS

| | | | |
|---|---|---|---|
| 2,889,848 | 6/1959 | Redmer | 137/315 |
| 3,314,371 | 4/1967 | Hopkinson | 103/148 |
| 3,994,294 | 11/1976 | Knute | 128/214 |
| 4,061,142 | 12/1977 | Tuttle | 128/214 |
| 4,080,967 | 3/1978 | O'Leary | 128/214 |
| 4,142,524 | 3/1979 | Jassawalla et al. | 128/214 |
| 4,155,362 | 5/1979 | Jess | 128/214 |
| 4,236,880 | 12/1980 | Archibald | 417/478 |
| 4,322,201 | 3/1982 | Archibald | 417/279 |
| 4,382,753 | 5/1983 | Archibald | 417/479 |
| 4,394,862 | 7/1983 | Shim | 604/67 |
| 4,397,642 | 8/1983 | Lamadrid | 604/245 |
| 4,496,351 | 1/1985 | Hillel et al. | 604/250 |
| 4,563,179 | 1/1986 | Sakai | 604/244 |
| 4,586,691 | 5/1986 | Kozlow | 251/7 |
| 4,689,043 | 8/1987 | Bisha | 604/250 |
| 4,927,411 | 5/1990 | Pastrone et al. | 604/65 |
| 4,932,629 | 6/1990 | Rodomista et al. | 251/4 |
| 4,944,485 | 7/1990 | Daoud et al. | 251/9 |
| 5,437,635 | 8/1995 | Fields et al. | 604/65 |

*Primary Examiner*—Wynn Wood Coggins
*Assistant Examiner*—Jennifer Maynard
*Attorney, Agent, or Firm*—John W. Montgomery; Gardere & Wynne, L.L.P.

[57] ABSTRACT

A medical tubing and slide clamp set is disclosed for use with a medical infusion pump designed for operation with a preselected medical tubing set having predetermined size and functional characteristics. The medical tubing and slide clamp includes a preselected medical tubing set having predetermined size and function characteristics. An opaque slide clamp is provided with a grasping end and a longitudinal clamp plate extending from the grasping end. The longitudinal clamp plate defines a clamp slot with a wide open portion sized for receiving the preselected medical tubing without closing the tubing, a narrow open portion sized for closing the tubing and a transition portion interconnecting the narrow and wide portions. A plurality of orifices are formed along the longitudinal clamp plate at predetermined locations arranged according to the size and functional characteristics of the medical tubing set. A receptacle formed in a medical pump includes a plurality of light sources and sensors mounted at predetermined positions for sensing the orifices or the absence of orifices to determine whether the size and functional characteristics of the tubing set will be proper for operation in the medical pump.

3 Claims, 4 Drawing Sheets

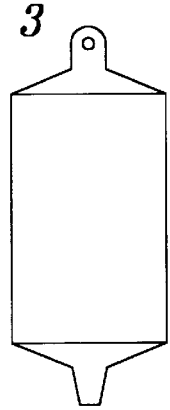
FIG. 3
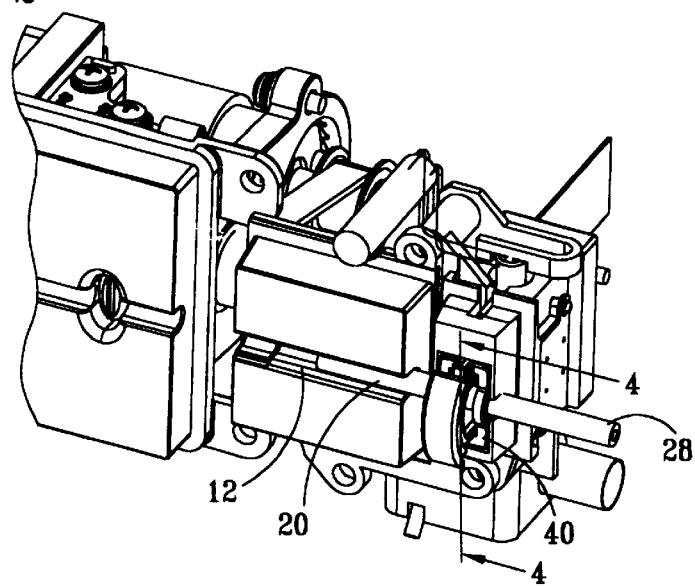
FIG. 2
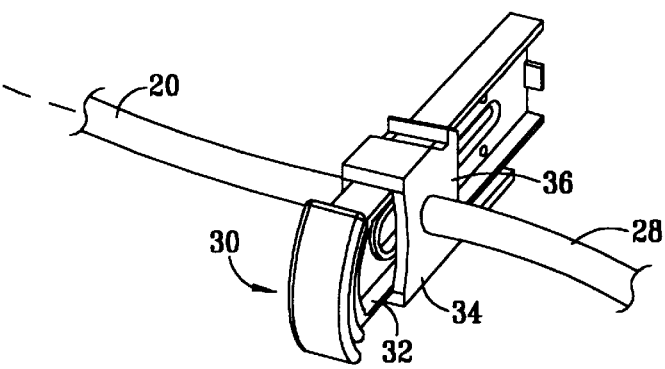
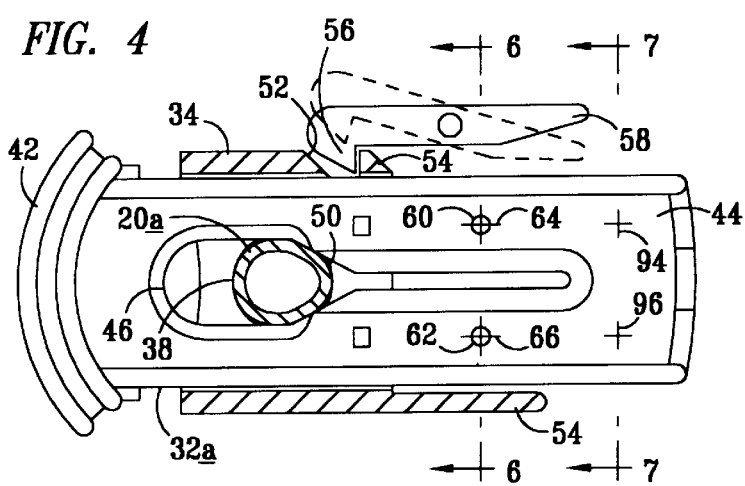
FIG. 4
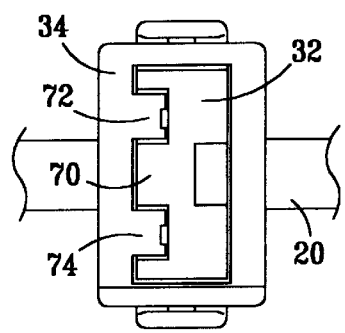
FIG. 5

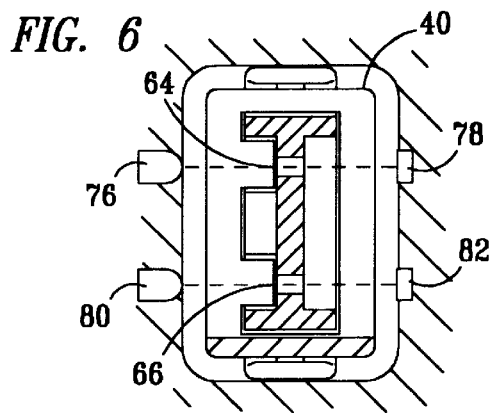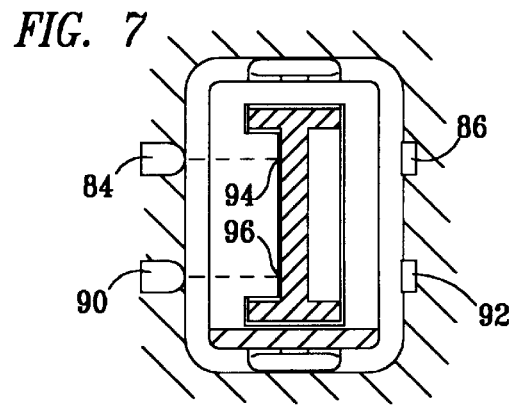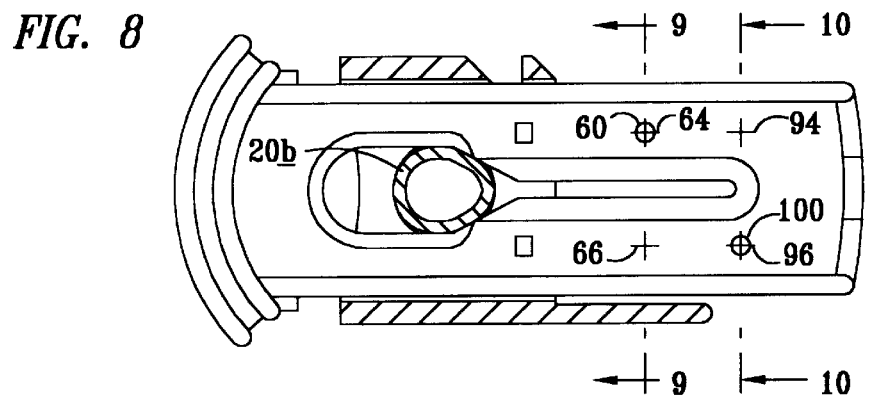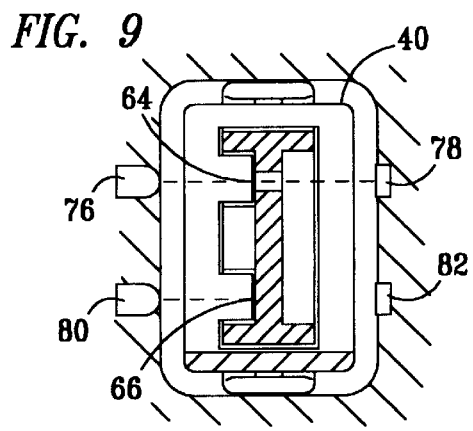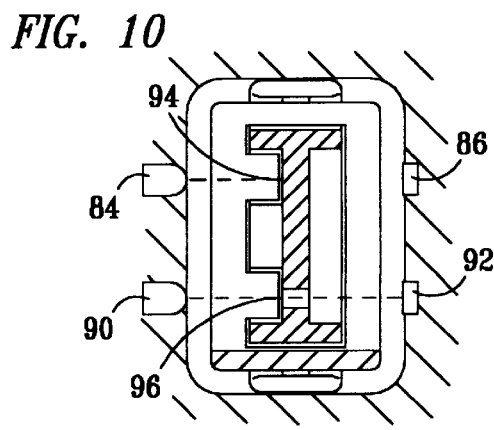

MEDICAL TUBING SLIDE CLAMP DEVICE FOR DETERMINING PROPER TUBING SIZE AND FUNCTIONAL CHARACTERISTICS

TECHNICAL FIELD OF THE INVENTION

The present invention relates to a slide clamp for a disposable medical infusion cassette or tubing set, particularly to a safety slide clamp to prevent free-flow when the disposable cassette or tubing set is disconnected from a medical infusion administration device, and more particularly to a slide clamp having structure for cooperation with sensory apparatus on the infusion administration device for determining proper size and functional characteristics of the cassette or tubing set to which the slide clamp is secured.

BACKGROUND OF THE INVENTION

Infusion of fluids, such as drugs and plasma, into a patient is desirable in the medical field. Two common infusion methods are intravenous delivery of fluids by gravity and either intravenous or in arterial delivery by mechanically pressurizing the fluids for delivery to the patient using infusion pumps. Modern infusion pumps typically administer mechanical forces to the exterior a disposable device, such as a flexible plastic cassette or a flexible plastic tubing connected upstream to a medical fluid bag and downstream to the patient.

In a cassette type infusion pump, disposable cassettes have been advantageously employed for providing a simple disposable element in combination with a relatively straight-forward pumping action. The cassette for this type of pump typically has one or more interconnected pumping chambers, and input and output tubing. The cassette and tubing are placed into contact with the pump or a pumping mechanism so that the contents or medicinal fluid pumped through the cassette and tubing are maintained in a sterile condition.

In another type of infusion pump, the pumping mechanism engages directly onto the tubing acting thereon with sequential compression forces to move the fluid through the tubing to the patient. This is called a peristaltic pump. Once again, the tubing set connected to the desired supply of medicine is inserted into the pumping mechanism maintaining a sterile condition of the medicinal fluid. Maintenance of a sterile condition is facilitated by disposing of the medicinal tubing set and simply replacing it with a newly sterilized and filled set as additional quantities of fluid are to be infused or when a new medicine is provided to a new patient.

Thus, disposable infusion tubing sets and disposable cassette sets are currently the standard of the industry for infusion flow control, whether through cassette pumps or through peristaltic pumps. One prior cassette pump and safety flow clip was designed for receiving the safety flow clip attached to the output tubing of a disposable cassette. Such a device is disclosed in U.S. Pat. No. 5,437,635, inventors Fields, et al., issued Aug. 1, 1995. The flow clip was designed to permit the operator to stop flow of fluids through the disposable cassette whether it was in or out of the pump. Also the receiving mechanism and flow clip were designed such that the cassette or the tubing set could not be installed unless the safety flow clip was in place. Flow was automatically closed if the cassette was not held in the proper operable pumping position. The cassette could not be removed until the flow clip was closed. Still the safety clip on the cassette could be manually moved from closed to open flow when the cassette was removed from the pump. The cassette set was also installable into the pump whether the safety clip was closed or open.

Of concern with respect to medical infusion pumps, whether cassette pumps or peristaltic pumps, is that the pumping capability and the accuracy of the pumps can depend in large part upon the size and functional characteristics of the cassette or tubing set. The functional characteristics can be affected by thickness, type of material, volume, resilience or any number of other features of the cassette or the tubing set. Thus, the use of one pumping cassette or one tubing set having particular size and functional characteristics can be properly calibrated for accurate, safe and controlled pumping and the use of another set with different size or different functional characteristics can be improper, inaccurate and possibly dangerous to the patient, unless the pumping parameters are appropriately adjusted to the different size and functional characteristics. Currently there is no known device or system that might automatically prevent such mismatching. The industry is currently relying on the ability of operators to distinguish size and on labeling and the competency of the operators to avoid this potentiality.

SUMMARY OF THE INVENTION

Thus, what has been invented is a slide clamp device for use on disposable medical infusion sets used with a medical infusion pump designed for operation with a flexible flow tube of the infusion set, having predetermined size and functional characteristic. The slide clamp device comprises a slide clamp body and a tube carrier. The tube carrier is insertable over the slide clamp body and the medical flow tube is secured to the tube carrier. The flow tube is either fastened to a cassette or integrally formed with the tubing set having predetermined size and function characteristic. The tubing is thus secured through the slide clamp to the tubing carrier so that neither can be removed from its engagement with the preselected infusion set having predetermined size and function characteristics whether the tubing set or the cassette set. The slide clamp comprises a grasping end attached to an opaque clamp plate. The clamp plate extends longitudinally from the grasping end. The clamp plate defines a clamp slot with a wide-open portion sized for receiving the flow tube without closing the tube, a narrow open portion sized for closing the flow tube and a transition portion interconnecting the wide and narrow portions such that movement of the clamp body relative to the tube moves the tube through the transition from open to closed or from closed to open depending upon the direction of relative movement. Further, according to the invention, a plurality of orifices are formed along the longitudinal clamp plate at predetermined positions arranged according to the size and functional characteristics of the tubing or cassette. The pump is provided with an engagement mechanism for the slide clamp having sensors for detecting the existence or absence of orifices at the predetermined locations. In the case of the plurality of the orifices, miniature light emitters are mounted at one inside wall of the engaging mechanism and adjacent receptors are mounted at the opposite inside wall of the engaging mechanism so that with the flow clip properly engaged in the receptacle, the existence of orifices at particular ones of the plurality of predetermined locations is sensed. The sensor data is communicated to pump control circuitry to allow the pump to operate according to the predetermined size and functional characteristics indicated by the location of the plurality of orifices.

In an alternative embodiment the pump may be designed with the capability for changing programming for pumping operation, so that a plurality of separate sets of cassettes or flow tubing, each having different size or functional characteristic may be properly operated by the same pump. A flow clip for each of the preselected different variations of size and/or functions of tubing sets or pumping cassettes for which the pump is programmed would have orifices through the opaque flow clip plate at different orientations or different locations. Upon insertion of the flow clip assembly into the receptacle, a plurality of sensors, arranged at a plurality of positions in the walls of the receptacle will sense the different orientations or different combinations of orifice positions in the flow clip and it will be identified electronically by pump control circuitry. The pump control circuitry activates separate sets of control parameters depending upon the locations of the orifices through the flow clip inserted into the receptacle. Thus, with the invention of a flow clip with a plurality of detectable orifices one pump can be preprogrammed to operate only with identified flow clips signifying proper size and function or characteristics and also to operate differently for different identified tubing sets or different identified cassettes.

BRIEF DESCRIPTION OF THE DRAWINGS

A more complete understanding of the invention may be had by reference to the following detailed description and claims, when taken in conjunction with the accompanying drawings, in which like numerals represent like elements and wherein;

FIG. 2 is a schematic partial cutaway perspective view of the pump and a flow clip engagement receptacle of FIG. 1;

FIG. 3 is a schematic representation of a disengaged flow clip and preselected tubing set positioned for insertion into the pump receptacle of FIG. 2;

FIG. 4 is a partial cross-sectional side view of a slide clamp, tube carrier, and tubing set according to one embodiment of the present invention depicting a plurality of orifices in the elongated body of the slide clamp;

FIG. 5 is a schematic end view of the slide clamp assembly of FIG. 4;

FIG. 6 is a partial cross sectional view taken along section line 6—6 of the slide clamp of FIG. 4, showing a slide clamp inserted within a receptacle and light sources and sensors positioned at predetermined locations;

FIG. 7 is a partial cross sectional view taken along section line 7—7 of the slide clamp of FIG. 4 inserted in a receptacle of a pump showing additional sensors positioned at additional predetermined locations;

FIG. 8 is a partial cross-sectional side view of an alternative embodiment of a slide clamp, tube carrier, and tubing set according to the present invention in which a tubing having preselected size and functional characteristics different from the size and functional characteristics of FIG. 4, is depicted showing a different arrangement of a plurality of orifices through the body of the slide clamp;

FIG. 9 is a partial cross sectional view of the slide clamp of FIG. 8 taken along section line 9—9;

FIG. 10 is a cross sectional view of the slide clamp of FIG. 8 taken along section line 10—10.

DETAILED DESCRIPTION OF THE PREFERRED EMBODIMENTS

Figure 1:
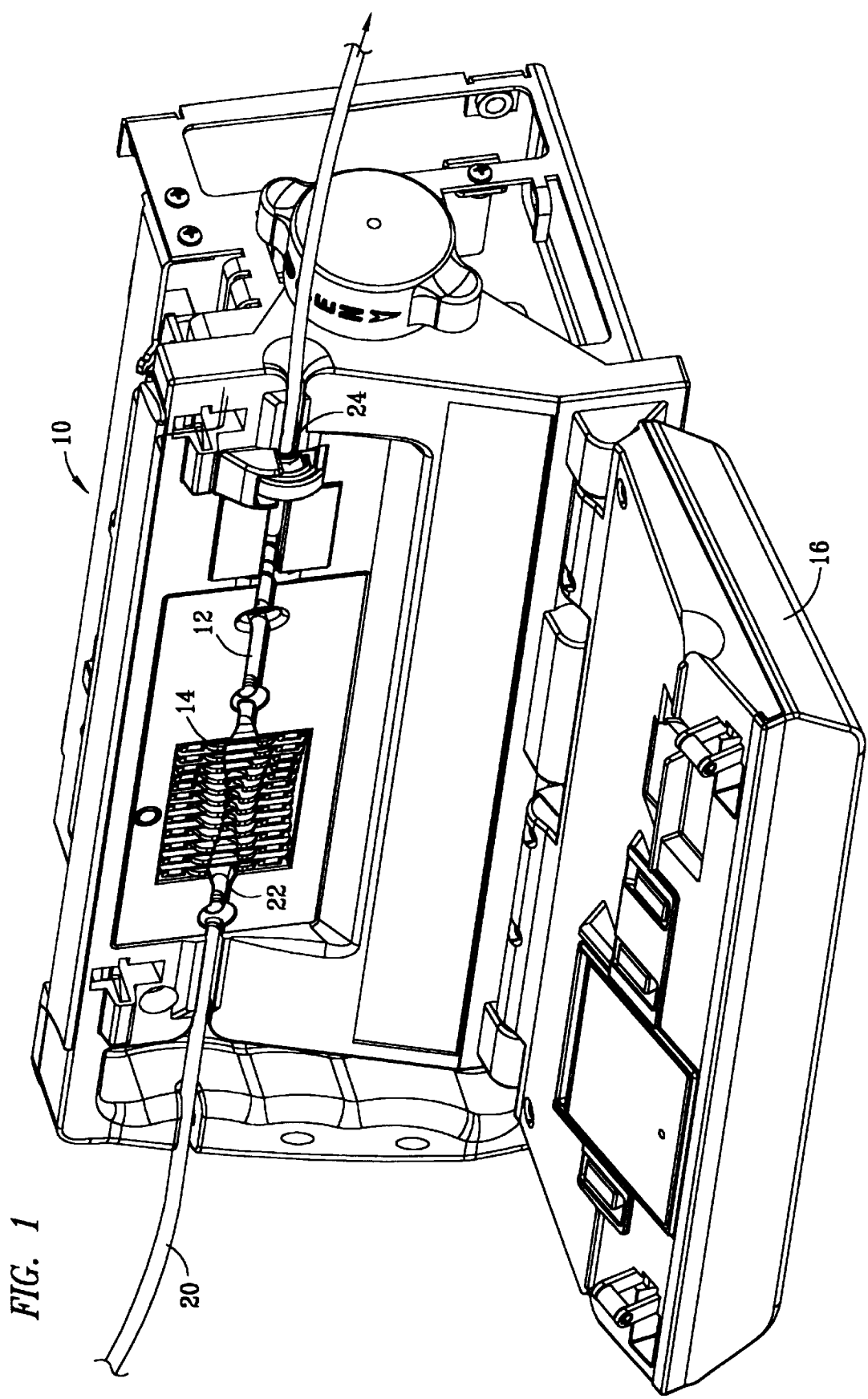
FIG. 1 is a perspective view of a representative infusion pump with a tubing set including a tubing, a tube carrier and flow clip engaged on a receptacle in the pump.

FIG. 1 depicts a schematic prospective view of a medical infusion pump 10 having a channel 12 formed in pump face 18 along which a channel 12 tubing set 20 is inserted and door 16 is closed so that a pump engagement portion 22 of the tubing set is engaged in a pumping apparatus 14 of the pump 10. The tubing set 20 further comprises an inlet end 24 typically attached to a source of fluid to be pumped 26 such as a medicinal fluid, a saline solution, a sucrose solution, any antibiotic or the like. There is also an outlet end 28 of the tubing that will be attached to a device, such as a needle, catheter or other such device for administering the pump fluid to a patient. Adjacent to the pump engagement portion 22 a flow clip set 30 is attached including a slide clamp 32 and a tube carrier 34. The flow clip set is assembled on the tubing set by sliding the slide clamp into the tube carrier, inserting the tubing through both the slide clamp and tube carrier and securing the tubing to the tube carrier. This procedure is accomplished in the sterile environment of the manufacturing facility so that the flow clip set, including both the slide clamp and the tube carrier are affixed to a particular tubing set that are sterilized and provided for use with the pump in a closed sterilized package. The tubing set and the flow clip set depicted in FIG. 1 are shown in an engaged position with the pump engagement portion of the tubing 22 inserted into channel 12 and with the flow clip set inserted into a receptacle 40 formed in the pump along channel 12 for receiving the slide clamp and tube carrier and engaging the tube carrier.

FIG. 2 shows a partial cutaway view of the pump 10 showing a portion of channel 12 along which the receptacle 40 is positioned.

FIG. 3 is a perspective view of one embodiment of the tubing set 20, including the flow clip set 30 with the tube carrier 34 affixed to the tubing 20 at a hole 36 formed through tube carrier 34.

As will be more fully understood with reference to FIGS. 3 and 4 in which FIG. 4 is a side view of the slide clamp 32 and a partial cross sectional view of the tube carrier 34 and tube 20 attached thereto, the slide clamp 32 comprises a grasping head 42 connected to, and preferably integrally formed with a longitudinal insertion plate 44 having a first large opening 46, a narrow slot 48 and a transition portion 50 interconnecting between said large opening 46 and said narrow slot 48. The large opening 46 is formed sufficiently large to allow a tubing 20 to pass there through without constricting the tubing. The slot 48 is sufficiently narrow (for example less than two times the wall thickness of tubing 20) to completely close the internal tubing 20. Movement of the slide clamp 32 relative to tubing 20 causes tubing 20 to move between an open position extending through large opening 46 or a closed position track between narrow slot 48. The tubing slides between those two positions along the angle of transition portion 50 when the slide clamp is moved relative to the tubing. The tubing is securely held in carrier 34 as by inserted through orifices 36 and 38 (orifice 36 shown in FIG. 3 and orifice 38 shown in FIG. 4). Carrier 34 is constructed with an engagement notch 52 along a top portion thereof and an angle ramp portion 54 so that a hook 56 on a pivotable engagement arm 58 easily raises up along ramp 54 upon insertion of the flow clip set into the receptacle and engages into notch 52. The arm 58 is prevented from pivoting upward out of notch 52 when the slide clamp 32 is moved inward such that tube 20 is in the large opening 46. Thus, the slide clamp must be moved outward relative to tubing 20 and the tube carrier 34 so that tubing 20 moves into narrow slot 48 before arm 58 may pivot upward and out of notch so that hook 56 is moved upward out of notch 52. Thus, the flow clip cannot be removed unless the tubing is in an "off" position, thereby avoiding uncontrolled flow when the tubing is not engaged in the pump.

A plurality of orifices 60 and 62 are shown formed at predetermined locations through an opaque plate 44 so that light can pass through orifices 60 and 62. FIG. 5 is an end view of the flow clip assembly 30, showing the flow clip engaged in an appropriate orientation on the slide clip. Proper orientation is maintained through the use of a tab 70 on the flow clip projecting from one side of plate 44 and complementary projections 72 and 74 from the inside wall of carrier 34.

FIG. 6 is a partial cross sectional view of the flow clip assembly 30 and also the receptacle 40 taken along a section line 6—6 at the position shown in FIG. 4. Upon full insertion, the tube carrier 34 becomes engaged at notch 52 with hook 56 so that tube 20 is in the large opening portion 46 and flow can proceed. When the clamp is fully inserted the pumping mechanism may normally be activated. Control circuitry prevents activation of the pumping mechanism and will not allow pumping unless full insertion of the slide clamp is detected. According to one aspect of the invention, a first light source 76, of a plurality of light sources such as a miniature LEDs, is mounted at a predetermined position on the inside wall of receptacle 40. First light source is aimed at a first sensor 78, of a plurality of sensors such as a photoelectric cells, mounted on the opposite inside wall of receptacle 40 at a predetermined position. The predetermined positions of the light source 76 and the sensor 78 are aligned with a predetermined location 64 of orifice 60, when the flow clip assembly is fully inserted into the receptacle. A second light source 80 and a second sensor 82 are also provided at adjacent positions corresponding to and aligned with location 66 of orifice 62. According to an aspect of the invention the pump will also be prevented from operating and/or an alarm will be given unless the plurality of sensors 78 and 82 determine that the plurality of orifices 60 and 62 are in proper predetermined locations to indicate that the size and function characteristics are appropriate for the operating parameters of the pump.

With reference to FIG. 7, it will be further understood that additional light sources 84 and 86 and sensors 88 and 90 are advantageously provided at the inside side walls of receptacle 40 corresponding to additional locations 94 and 96 of plate 44 at which no orifices have been formed to allow light to be transmitted there through. Thus, a plurality of sensors are provided for sensing the proper location of a a plurality of orifices. The absence of orifices at predetermined locations is also detected to confirm the existence of specifically located orifices rather than large nonspecifically located voids or openings in the slide clamp. In the embodiment depicted in FIG. 4 the size of tubing 20 and its functional characteristics are determined in part by, for example the wall thickness of the tubing. Thus, the formation of a plurality of orifices 60 and 62 at the locations 64 and 66 without forming orifices at location 94 and 96 provide the pump with sensory input from the plurality of sensors 78, 82, 86 and 92. This data as provided by orifices 60 and 62 formed at predetermined locations 64 and 66, and the absence of orifices at locations 94 and 96 is coordinated during manufacture with the particular size and functional characteristics, in this particular instance the thin walled tubing characteristic of tubing 20. Only tubing sets having the same, or operationally compatible, size and functional characteristics will be affixed to a slide clamp for the pump having the orifices formed in the locations 64 and 66.

The advantage of a plurality of orifices through the body of slide clamp 32 may be further had with reference to FIG. 8, in which an alternative tubing 20B having a thicker wall than tubing 20A of FIG. 7 is depicted. The construction of slide clamp 32B is substantially similar to that of 32A of FIG. 4, except that the plurality of orifices formed in slide clamp 32B comprise an orifice 60 at location 64 and an orifice 100 at location 96. There is an absence of an orifice at location 66 and at location 94. The size and functional characteristics of the thicker wall tubing 20B (compared to tubing 20A of FIG. 7) are different and as such slide clamps 32B having a plurality of orifices located at a different predetermined locations will be coordinated only with tubing sets having those size and functional characteristics.

It will be understood, with reference to FIG. 9, which is a partial cross sectional view taken along section line 9—9 through location 64 and 96, that light transmitted from light source 76 to sensor 78 precedes through orifice 60, however, no light from source 80 is transmitted to sensor 82. Referring also to FIG. 10 the light that would have been blocked by slide clamp 32A from light source 90 will be transmitted through the orifice 100 to sensor 92, thus, the construction of the slide plate with the plurality of orifices corresponding to locations of a plurality of sensors, which location are predetermined by the size and function characteristics of the tubing provides a unique and unobvious advantage of allowing the pump to receive data from a plurality of sensors 78, 82, 86 and 90 to which sensation data can be used by the pump to determine the size and function characteristics of the preselected tubing set indicated by the tubing set indicated by the position of the orifices.

When three sensors are used there are three different combinations of locations for two orifices. It has been found advantageous to have two orifices and two closed locations in the flow clamp, so that the six different size and function characteristics can be determined. Additional sensors can provide additional combinations of at least two open orifice locations so that additional different size and function characteristics can be determined.

Figure 11:
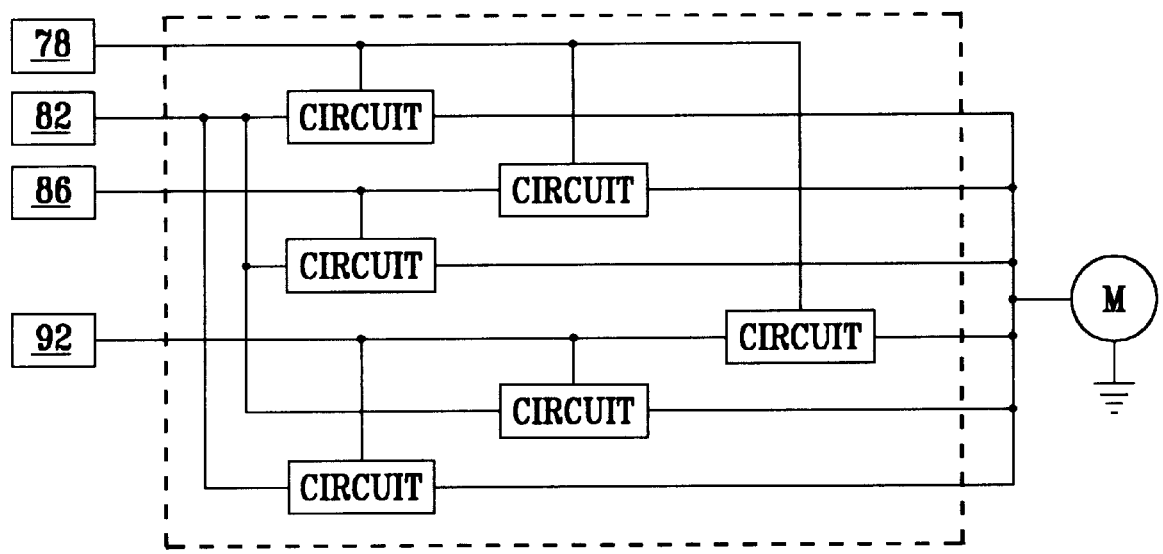
FIG. 11 is a schematic control circuit diagram depicting sensory determination of proper size and functional characteristics based upon orifice locations in a slide clamp of a cassette or tubing set and for operating a pump accordingly.

The circuitry by which the sensory data is operationally connected to the pumping mechanism, so that the operational parameters of the pump are appropriately modified according to the sensory data is schematically depicted in FIG. 11. Thus, depending on the appropriateness of the position of orifices, the pump may lock out any operation, for example, where a plurality of orifices are not detected at any location of a plurality of locations or "orifices" are detected at all locations. A slide clamp having an opaque plate without having the predetermined orifices would indicate that a particular size and function characteristic of tubing was not predetermined at the factory. Thus, unselected tubing not preselected for safe size and function would not be inadvertently used in the pump. Another example may be where a slide clamp is transparent or where orifices are at all sensory locations, the pump may discontinue operation as being an unrecognized or undetermined tubing set. Where the locations are as in FIG. 4, orifices 60 and 62, so that sensory input is received from sensory 78 and 82, the pump operation is controlled through a first circuit 102 and processor circuit 104. The processor circuit 104 may activate the pumping mechanism 106 according to one set of parameters. The sensory input from sensors 78 and 92 may operate through circuit 108 to activate the pump motor 106 according to another set of parameters in microprocessor 104. As for example, pumping faster to obtain the same volume of flow through the small inside diameter of tubing 20B compared to the rate of pumping to obtain that same flow for the large inside diameter of tubing 20A. Similarly, any of the six plurality of combinations of two orifices can produce operation according to a set of parameters proper for the size and function characteristics as determined by the location of the plurality of orifices.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. A mechanism for a medical pump for determining proper size and functional characteristics of a medical tubing said mechanism comprising:

(a) a medical tubing having predetermined size and functional characteristics;

(b) an opaque slide clamp comprising a grasping end, a longitudinal clamp plate extending from said grasping end, said longitudinal clamp plate defining a clamp slot with a wide open portion sized for receiving said medical tubing without closing said medical tubing, a narrow open portion sized for closing said medical tubing and a transition portion interconnecting said narrow and wide portions of said clamp slot;

(c) a plurality of orifices formed along said longitudinal clamp plate at predetermined locations arranged according to said size and functional characteristics of said medical tubing;

(d) a receptacle held in a medical pump medical pump constructed for receiving said slide clamp, said receptacle including spaced apart inside walls;

(e) first and second light sources mounted on one of said inside walls and aligned sensors on the other end of said inside walls at predetermined positions corresponding to the predetermined locations of said plurality of orifices in said slide clamp when said slide clamp is received into said receptacle for sensing the existence of orifices at said predetermined locations;

(f) a circuit operatively coupled to said pump and said sensors for permitting operation of said pump only when said plurality of orifices are sensed at said predetermined positions.

2. The mechanism of claim 1 wherein said plurality of orifices comprise two orifices formed at two predetermined locations selected from at least three predetermined locations on said opaque slide clamp.

3. The mechanism of claim 1 wherein said plurality of orifices comprise two orifices formed at two predetermined locations selected from at least four predetermined locations on said opaque slide clamp.

* * * * *